United States Patent
Mallouk et al.

(10) Patent No.: US 6,913,849 B2
(45) Date of Patent: Jul. 5, 2005

(54) METHOD OF SCREENING COMPOSITIONS FOR ELECTROCATALYTIC ACTIVITY IN A GAS DIFFUSION ELECTRODE

(75) Inventors: Thomas E. Mallouk, State College, PA (US); Eugene S. Smotkin, Chicago, IL (US); Benny C. Chan, State College, PA (US); Guoying Chen, State College, PA (US); Renxuan Liu, Chicago, IL (US)

(73) Assignee: UOP LLC, Des Plaines, IL (US)

( * ) Notice: Subject to any disclaimer, the term of this patent is extended or adjusted under 35 U.S.C. 154(b) by 198 days.

(21) Appl. No.: 09/899,767

(22) Filed: Jul. 5, 2001

(65) Prior Publication Data

US 2002/0014584 A1 Feb. 7, 2002

Related U.S. Application Data

(60) Provisional application No. 60/216,931, filed on Jul. 8, 2000.

(51) Int. Cl.[7] ............................. H10M 8/10; C12M 1/34
(52) U.S. Cl. ............................. 429/30; 429/12; 429/32; 429/40; 204/410; 204/403.03; 204/422; 204/424; 435/4; 435/287.1; 435/287.8
(58) Field of Search ...................... 204/403.02, 403.03, 204/409, 410, 411, 421, 422, 424, 426, 432, 403.2, 403.3; 429/30, 32, 40, 12, 22; 435/4, 287.1, 287.8

(56) References Cited

U.S. PATENT DOCUMENTS

| | | | | |
|---|---|---|---|---|
| 5,683,829 A | * | 11/1997 | Sarangapani | 429/42 |
| 5,922,617 A | | 7/1999 | Wang et al. | 436/518 |
| 6,063,633 A | | 5/2000 | Willson, III | 436/37 |
| 6,187,164 B1 | * | 2/2001 | Warren et al. | 205/81 |
| 6,333,196 B1 | | 12/2001 | Willson, III | 436/37 |
| 6,528,191 B1 | * | 3/2003 | Senner | 429/12 |
| 6,692,856 B2 | * | 2/2004 | Smotkin | 429/30 |

* cited by examiner

*Primary Examiner*—Padmashri Ponnaluri
*Assistant Examiner*—My-Chau T Tran
(74) *Attorney, Agent, or Firm*—John G. Tolomei; Frank S. Molinaro; Maryann Maas

(57) ABSTRACT

A novel process and apparatus to combinatorially screen a large number of discrete compositions for electrocatalytic activity have been developed. The apparatus contains a cell body adjacent to a fluid permeable catalyst array support supporting multiple solids. A catalyst mask having holes that are in alignment with the multiple locations for supporting solids is placed over the catalyst array support, masking the solids. A cell cover is positioned adjacent to the catalyst array support, with the cell cover having a passage for monitoring the solids through the mask. A detector may be in alignment with the passage of the cell cover.

12 Claims, 3 Drawing Sheets

METHOD OF SCREENING COMPOSITIONS FOR ELECTROCATALYTIC ACTIVITY IN A GAS DIFFUSION ELECTRODE

CROSS REFERENCE TO RELATED APPLICATION

This application claims the benefit of priority of co-pending U.S. Provisional Application No. 60/216,931 filed Jul. 8, 2000.

STATEMENT REGARDING FEDERALLY SPONSORED RESEARCH OR DEVELOPMENT

This invention was made under the support of the United States Government, Department of Commerce, National Institute of Standards and Technology (NIST), Advanced Technology Program, Cooperative Agreement Number 70NANB9H3035. The United States Government has certain rights in the invention.

FIELD OF THE INVENTION

This invention relates to an apparatus for screening compositions for electrocatalytic activity in gas diffusion electrodes.

BACKGROUND OF THE INVENTION

Fuel cells provide increased efficiency and energy density relative to internal combustion engines and secondary batteries. By converting chemical energy directly into electrical energy, less thermal waste is created than in a heat engine, see Bockris, J. O. 'M; Srinivasan, S. Fuel Cells: Their Electrochemistry; McGraw Hill: New York, 1969. While hydrogen fuel cells are efficient and may become a major source of energy in the next millennium, they are not practical for all purposes. The infrastructure for distribution of hydrogen is not well developed, as it is for liquid and gaseous hydrocarbon fuels, and the latter present clear advantages for transportation, home power generation, and remote power applications.

Reforming of fossil fuels can provide a route for their use in hydrogen-air fuel cells:

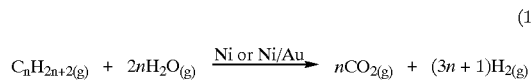

(1)

The hydrogen evolved from the reforming process can be used in well known air breathing polymer electrolyte membrane (PEM) fuel cells which perform the following half-cell reactions:

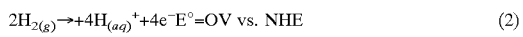

(2)

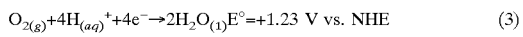

(3)

The anode catalysts used in reformate gas fuel cells are simple alloys and metals such as platinum and platinum-ruthenium alloy. After steam reforming and subsequent fuel processing steps, low-temperature water gas shift and partial oxidation of the fuel, a small amount of carbon monoxide, 10–100 ppm, is still present. The anode catalyst is quickly poisoned by the carbon monoxide and thereby rendered inoperable. Therefore, with current catalysts, the reformate gas requires an additional purification step such as pressure-swing adsorption to remove the carbon monoxide. However, the purification process and equipment greatly adds to the weight and expense of the overall fuel cell system. Another solution is to find effective catalysts that rapidly oxidize or that are not poisoned by carbon monoxide.

There is presently no reliable theory for predicting the catalytic behavior of ternary and higher alloys, or even for predicting equilibrium phase behavior of four- and five-component systems. When predictions are difficult, an attractive alternative is the Edisonian approach to the problem. The historical Edisonian approach has the drawbacks of being laborious and time intensive. To improve the efficiency of the Edisonian approach, combinatorial applications have been developed. Combinatorial methods have been used extensively in biorganic systems, but to date have been applied to only a few inorganic materials applications. Some of these include: alloy superconductors (Hanack, J. J. J. Mat. Sci., 1970, 5, 964); superconducting and magnetoresistive metal oxides (Xiang, X.-D.; Sun, X.; Briceño, G.; Lou, Y.; Wang, K.-A.; Chang, H.; Wallace-Freedman, W. G.; Chen, S. -W.; Schultz, P. G.; Xiang, X-D. Science, 1995, 268, 1738; Briceño, G.; Chang, H.; Sun, X.; Schultz, P. G. Science, 1995, 270, 273); hydrogenation catalysts (Moates, F. C.; Somani, M.; Annamalai, J.; Richardson, J. T.; Luss, D.; Willson, R. C. Ind. Eng. Chem. Res., 1996, 35, 4801); phosphors (Danielson, E.; Devenney, M.; Gianquinta, D. M.; Golden, J. H.; Haushalter, R. C.; McFarland, E. W.; Poojary, D. M.; Reaves, C. M.; Weinberg, W. H.; Wu, X. D. Science, 1998, 279, 837); and nanoparticle substrates for surface enhanced Raman spectroscopy (Baker, B. E.; Kline, N. J.; Treado, P. J.; Natan, M. J. J. Am. Chem. Soc., 1996, 118, 8721).

While many binary, a few ternary electrocatalysts (see Ley, K. L.; Liu, R. C.; Pu, C.; Fan, Q.; Leyarovski, N.; Segré, C.; Smotkin, E. S. J. Electrochem.Soc., 1997, 144, 1543) and a few electrocatalysts (see Danielson, E.; Devenney, M.; Gianquinta, D. M.; Golden, J. H.; Haushalter, R. C.; McFarland, E. W.; Poojary, D. M.; Reaves, C. M.; Weinberg, W. H.; Wu, X. D. Science, 1998, 279, 837) have been investigated for fuel cells, it is anticipated that the combinatorial apparatus of the present invention would result in the discovery of new electrocatalysts.

In a serial evaluation program, the effectiveness of an electrocatalyst is determined by measuring the current density as a function of potential. For combinatorial screening, the traditional method becomes increasingly unwieldy as the number of components increases. The traditional technique also suffers from the fact that most of the phase space from which data is collected is not interesting for electrocatalysis. An indirect, optical screening method was therefore developed that allows simultaneous testing of hundreds of different compositions and pinpointing of the best catalysts, see WO 00/04362. The oxidation of hydrogen generates protons at the electrode surface. In an unbuffered solution, the local pH in the diffusion layer drops considerably with the generation of protons, even at relatively low current density. When the potential of the array is swept slowly from cathodic to anodic potentials, the best catalysts generate protons first. A fluorescent acid-base indicator can be used to detect the catalysts that most efficiently oxidize methanol by screening for regions that luminesce directly above the electrode. An indicator that may be used for these experiments, N-3-pyridin-2-yl-<4,5,6>-triazolo-<1,5-a>-pyridine (PTP, $Ni^{2+}$ complex), fluoresence light blue in its acidic form but does not fluoresce in its basic form, see Mori, H; Sakamoto, K.; Mashito, S.; Matsuoka, Y.; Matsubayashi, M.; Sakai, K. Chem.Pharm. Bull., 1993, 41, 1944.

The present invention provides an improved apparatus for use with, for example, the above-described optical screening method of evaluating electrocatalytic activity of a plurality of solid catalysts. By employing a diffuser, the improved apparatus allows a gaseous reagent to be more evenly distributed across an array of catalysts. Through using a reagent mask, reagent is channeled into contact with the catalysts being evaluated, and through using a catalyst mask, interfering background signal and convection of the solution in contact with the catalysts is minimized. The apparatus of the present invention may be employed in methods beyond those described above.

SUMMARY OF THE INVENTION

One purpose of the present invention is to provide a novel apparatus to combinatorially screen a large number of discrete compositions for electrode catalysts. The apparatus contains a cell body having a fluid inlet and preferably a fluid outlet. A fluid permeable catalyst array support is positioned adjacent to the cell body, with the catalyst array support having multiple locations for supporting solids. A catalyst mask is positioned adjacent to the catalyst array support, with the catalyst mask having holes that are in alignment with the multiple locations for supporting solids of the catalyst array support. A cell cover is positioned adjacent to the catalyst array support, with the cell cover having a passage for monitoring the solids. A detector is in alignment with the passage of the cell cover.

Another purpose of the present invention is to provide a novel method for screening an array of solids for electrocatalytic activity. The method begins with depositing the solids of the array on a catalyst array support. Then a catalyst mask is placed over the catalyst array support, with the mask having holes in the same pattern as the solids of the array. The solids on the catalyst array support and masked by the catalyst mask are contacted with a reagent fluid and a fluid containing an ion concentration indicator. A potential is applied to the catalyst array support. Excitation radiation is impinged on the catalyst array support, and emission radiation emitting through the holes of the catalyst mask is measured. The electrocatalytic activity of the solids in the array is determined from the emission radiation measurements.

Still another purpose of the invention is to provide a bulk catalyst testing apparatus. The bulk catalyst testing apparatus contains a bulk cell body having a first and a second fluid inlet and a first and a second fluid outlet. An optional diffuser, such as a cloth disk may be positioned adjacent the bulk cell body in alignment with the first fluid inlet and the first fluid outlet. A fluid permeable bulk catalyst support structure having a catalyst thereon is positioned adjacent to the diffuser and bulk cell body and in alignment with the first fluid inlet and the first fluid outlet of the bulk cell body. A bulk cell cover is positioned adjacent to the catalyst support structure, with the bulk cell cover having a passage to allow for fluid contact with the catalyst.

Yet another purpose of the invention is to provide a method for testing a selected catalyst for electrocatalytic activity where the selected catalyst is deposited or synthesized on a first side of a bulk catalyst support structure and the bulk catalyst support structure is placed on a bulk cell base with a second side of the bulk catalyst support structure adjacent to and in alignment with a fluid inlet and a fluid outlet of the bulk cell body. The catalyst is covered with an electrolyte solution and is contacted with a reagent fluid that is passed through the fluid inlet adjacent the bulk catalyst support structure and through the bulk catalyst support structure. A series of different voltages is applied to the catalyst support structure and the current generated during each voltage is measured. Electrocatalytic activity is determined using the voltage and current measurements.

DETAILED DESCRIPTION OF THE INVENTION

Figure 1:
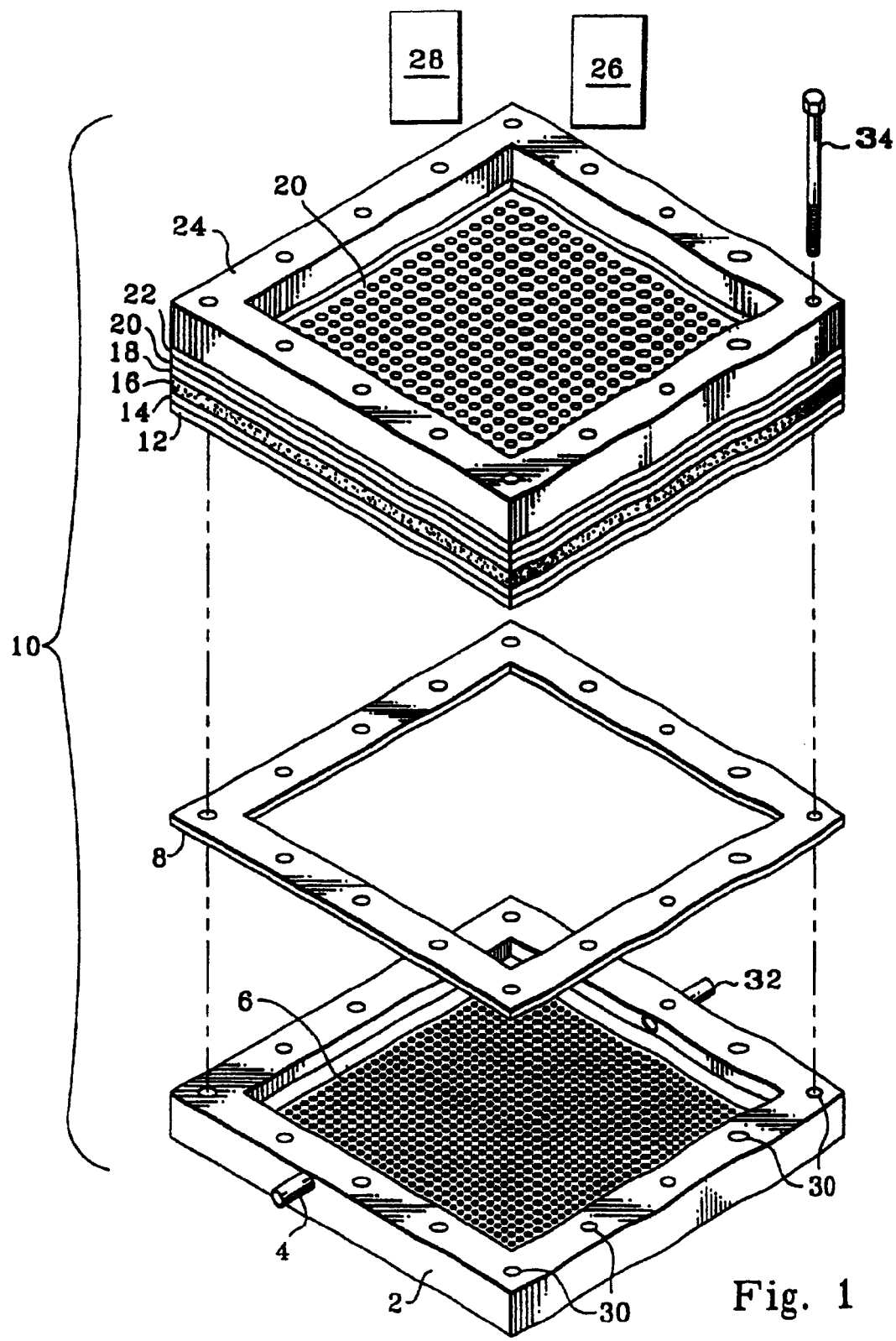
FIG. 1 is a generic view of a first embodiment of the combinatorial screening cell.

The present invention relates to the design of a new combinatorial screening cell and a method using the new cell to discover new electrocatalysts. The combinatorial screening cell offers several improvements over those previously disclosed. Two primary improvements in the apparatus of the present invention as compared to those in the art are the diffuser and the one or two masks. First, the diffuser allows a gaseous reagent to be distributed more evenly among the catalysts of the array, thereby allowing the comparison among the catalysts to be more accurate. Secondly, the reagent mask channels the reagent to the catalysts of the array and prevents the reagent from permeating across the entire surface of the catalyst support structure while the catalyst mask minimizes background interference and convection of the solution in contact with the catalysts. The cell may be used in a parallel, indirect, chemical method of detecting highly active electrocatalysts out of an array of tens to thousands of compositions. A single-electrode apparatus for the testing of bulk catalysts is also part of the present invention. The bulk test cell is used to analyze bulk quantities of active catalysts identified in the combinatorial process using current-voltage curves.

To better understand the apparatus of the present invention, one possible method in which the apparatus may be employed will first be briefly discussed. The example method involves several steps. Catalytic compositions to be tested are first deposited or synthesized on a porous, fluid permeable, conductive support. For example, an array of compositions may be prepared by applying the compositions of interest onto a carbon paper support. Alternatively, the compositions may be synthesized on the carbon paper by dissolving metal salts and applying the solution to the carbon paper using a robotic plotter such as Cartesian Technologies, PixSys 3200. It is preferred that the completed array contains the same number of moles of metal at each location. To prepare metal alloys, a preferred method is to add a chemical reducing agent such as borohydride, hydrogen gas, formaldehyde, hydroxylamine, or hydrazine. The arrays may be washed repeatedly with deionized water. Bulk catalysts may be prepared using the same chemical methods as with the arrays. The bulk catalyst is applied to a carbon support.

The array of catalysts is then placed in the combinatorial screening cell of the present invention. A reagent gas is introduced into the cell and allowed to diffuse before contacting the catalysts. In some applications, the reagent may be a liquid instead of a gas. A potential is applied to the catalyst array support to induce electrocatalytic activity, if present, in the catalysts. If a catalytic composition is active, protons are either consumed or produced in the vicinity of the catalyst which causes a change in the local pH. The change in local pH can be converted to a fluorescence signal by an indicator and an excitation source. Electrocatalytically active compositions may be optically identified using the fluorescence signal. This example method is described more fully in WO 00/04362, "Method of Screening Compositions for Electrocatalytic Activity." The compositions at the regions discovered to have higher activity can then be scaled up to allow detailed bulk sample current-voltage testing in the single-electrode gas diffusion cell. With the apparatus of the present invention, the above method is improved through the additional step of masking the catalysts of the array, and diffusing the reagent gas prior to contact with the catalysts, both of which will be discussed in more detail below.

Once formed on the catalyst array support, the array of catalysts is evaluated in the apparatus of the present invention. Turning to FIG. 1, the combinatorial array is shown placed within the overall screening cell 10 of the present invention. The cell body, 2, is made from an electrically insulating material such as, for example, Plexiglas. The cell body is shaped to form a chamber within the cell body. It is preferred that the cell body contains walls to form the chamber. Reagent fluid, which can be a gas, a mixture of gasses, or a liquid or mixture of liquids, enters cell body 2 via inlet 4 and is allowed to diffuse through the chamber formed by cell body 2. Excess reagent fluid may be removed from the cell body via outlet 32. Reagent fluid in the gaseous phase is diffused by diffuser 6. Any suitable diffuser may be used so long as the gas is more evenly distributed across the interior of the cell body. A preferred diffuser is a carbon cloth.

In the past, liquid fuels were most commonly used and a diffuser was not required. However, reformate fuel and other gaseous fuel cell reagents, such as oxygen, are not soluble in water and must be contacted with the catalysts in the gas phase. Attempts at introducing gaseous reagents provided unreliable results because the flow of reagent gas through the porous electrode structure (or catalyst array support) was not constrained to the specific locations of the catalyst deposits. The diffuser of the present invention operates to provide a more uniform flow of reagent gas across the array of catalysts thereby providing for more reliable results.

An optional reagent mask 12, which has an array of holes arranged to match the pattern of the array of catalysts on the catalyst array support, is located adjacent the diffuser. Adjacent the reagent mask is catalyst array support 16. Catalyst array support 16 is preferably carbon paper having been treated with Teflon™ on the side opposite the array of catalysts. It is preferred that the catalyst array support be treated on one side with a hydrophobic substance such as Teflon in order to prevent permeation of solution from one portion of the testing cell to another portion of the cell. The reagent mask is placed adjacent the treated side of the catalyst array support, and adjacent the untreated catalyst bearing side of the catalyst array support is catalyst mask 20. Like reagent mask 12, catalyst mask 20 has an array of holes that matches the pattern of the array of catalysts on the catalyst array support. It is preferred that the catalyst mask 20 is constructed of nonconductive material such as Plexiglas. Adjacent the catalyst mask is cell cover 24 which has a window or passage to allow for monitoring of the array of catalysts. An optional excitation source 26, or detector 28 may be aligned with the window or passage of cell cover 24. The excitation source may be a radiation source such as an ultraviolet radiation source, and the detector may be as simple as the human eye, or more complex such as analytical instrumentation. The catalyst array support traverses the cross section of the cell body and divides the apparatus into two portions. A first portion being defined as the portion between cell body 2 and the catalyst array support 16, and a second portion being defined as the portion between the catalyst array support 16 and the cell cover 24.

It is preferred that between each of the elements discussed above, a seal such as a gasket is used to seal the contact between the elements. It is also preferred that the gaskets are silicone gaskets, although other gaskets would also be suitable. In FIG. 1 the gaskets are shown as elements 8, 14, 18, and 22. Furthermore, it is preferred that the apparatus have at least one fastener to hold the elements together and in alignment. Suitable fasteners include screws or bolts and corresponding holes in the elements, shown as 34 and 30 in FIG. 1. Clamps or other fasteners may be successfully used.

In one embodiment of the invention, the first portion of the cell, the portion between cell body 2 and the catalyst array support 16, houses the chamber formed by the cell body, the diffuser, and the reagent mask. The diffuser operates to distribute gaseous reagent fairly evenly across the chamber of the cell body. The reagent mask then channels the reagent to the location of the catalysts on the catalyst array support. The reagent mask, while preferred, is optional. The reagent may be allowed to directly contact the surface of the catalyst array. The benefit of the reagent mask is that the reagent is forced to contact the catalysts of the array instead of being allowed to pass around the catalysts through the portions of the catalyst array support that contains no catalyst. Furthermore, the reagent mask and the catalyst mask together may achieve a reduction in background signal beyond that achievable using the catalyst mask alone. The reagent mask would operate to direct the reagent fluid to locations of the catalyst array support where the catalysts reside and block reagent fluid from contacting the catalyst array support at locations where no catalyst resides. The background signal generated at locations where no catalysts reside may be further reduced due to the lack of fluid reagent in those areas.

The second portion of the cell, defined as the portion between the catalyst array support 16 and the cell cover 24, houses the counter electrode, the reference electrode, and the electrolyte solution containing the fluorescent indicator, Ni-PTP or Phloxine B which is a base-fluorescent indicator used for cathode screening experiments. The catalyst array support is contacted using a piece of gold foil and made the working electrode of the three-electrode cell. If oxidation reactions are of interest, the potential is made incrementally more anodic. For reduction reactions, the potential is increased cathodically. An excitation source for the indicator, such as, for example, an ultraviolet light may be applied to the array. The most active catalysts begin to change the proton concentration at the lowest overpotential and the solution above these catalysts as defined by the catalyst mask begins to fluoresce. The catalyst mask forms wells to help contain solution within the area above each catalyst location and aids in the detection of discrete catalysts with high activity. The wells operate to minimize convection of the solution and dissipation of the signal. If the solution were not retained by wells formed by the catalyst mask, the indicator compound may be quickly swept away from the catalyst site perhaps resulting in a false low signal measurement. Having the wells allows for a greater relative contrast between the signal from the solution retained adjacent a catalyst and that of the background. Furthermore, without the catalyst mask, background fluorescence generated in areas surrounding the catalyst locations would hamper the detection of fluorescence resulting from catalyst activity.

Figure 2:
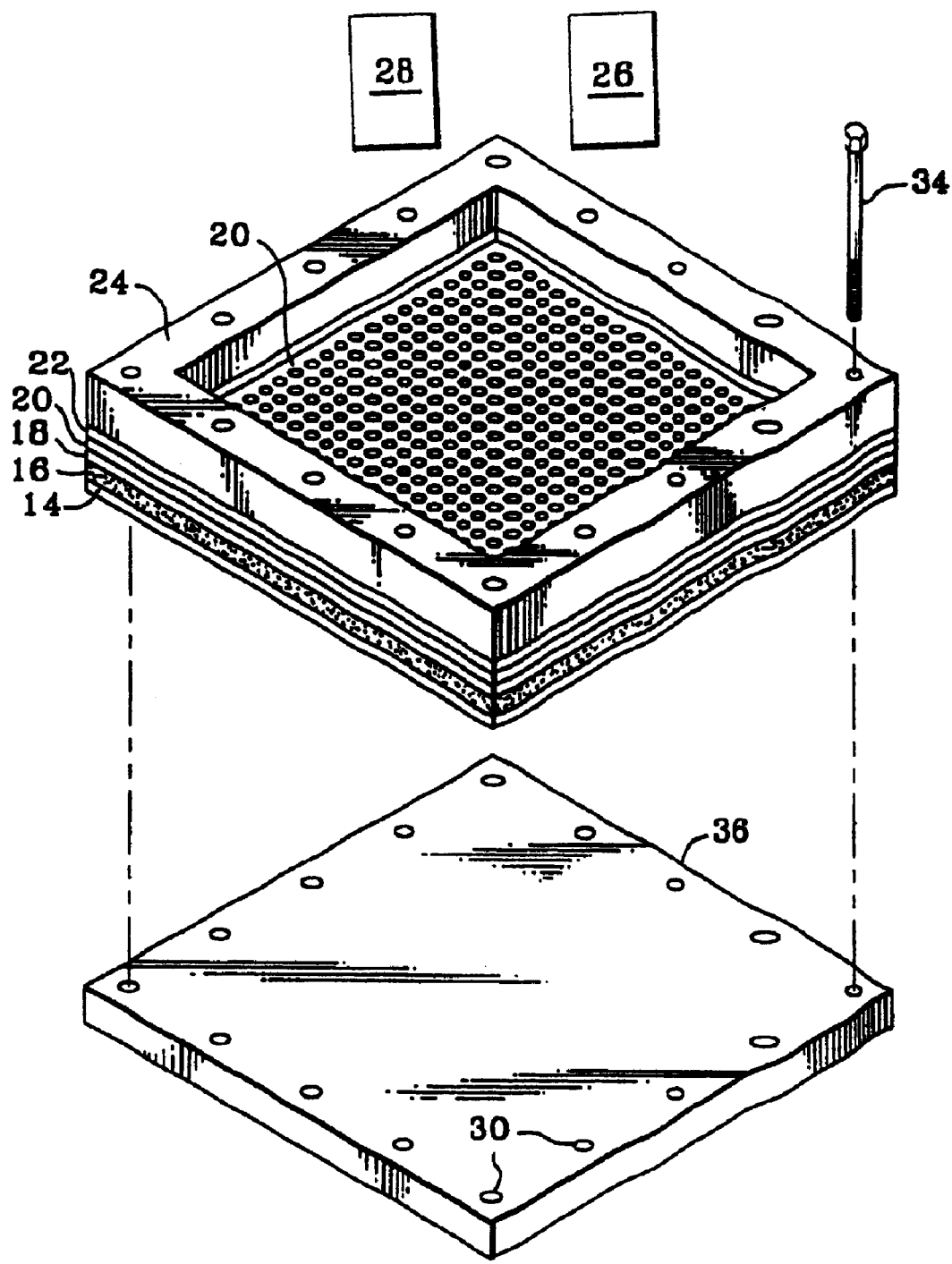
FIG. 2 is a generic view of a second embodiment of the combinatorial screening cell which is useful in applications where the reagent fluid and the solution containing the indicator are identical.

The combinatorial screening cell can be readily adapted for other electrochemical processes. For example, in some applications, there is no need for a gaseous reactant component, as in methanol oxidation. In a situation such as methanol oxidation, the cell body, the diffuser, and the reagent mask are not necessary and would be replaced by a catalyst array support backing. The backing is preferably a solid unit such as a sheet of Plexiglas. A seal may be placed between the backing and the catalyst array support. The purpose of the backing would be primarily to close the cell. In this embodiment of the invention, it is not necessary that the catalyst array support be fluid permeable. Furthermore, the liquid reagent and the fluid containing the indicator are identical. This embodiment is shown in FIG. 2 where catalyst backing 36 is positioned adjacent gasket 14. Catalyst array support backing 36 of FIG. 2 replaces cell body 2, diffuser 6, gasket 8, and reagent mask 12 of FIG. 1. The flexibility of the combinatorial screening cell allows a wide variety of electrochemical catalysts problems to be studied.

Figure 3:
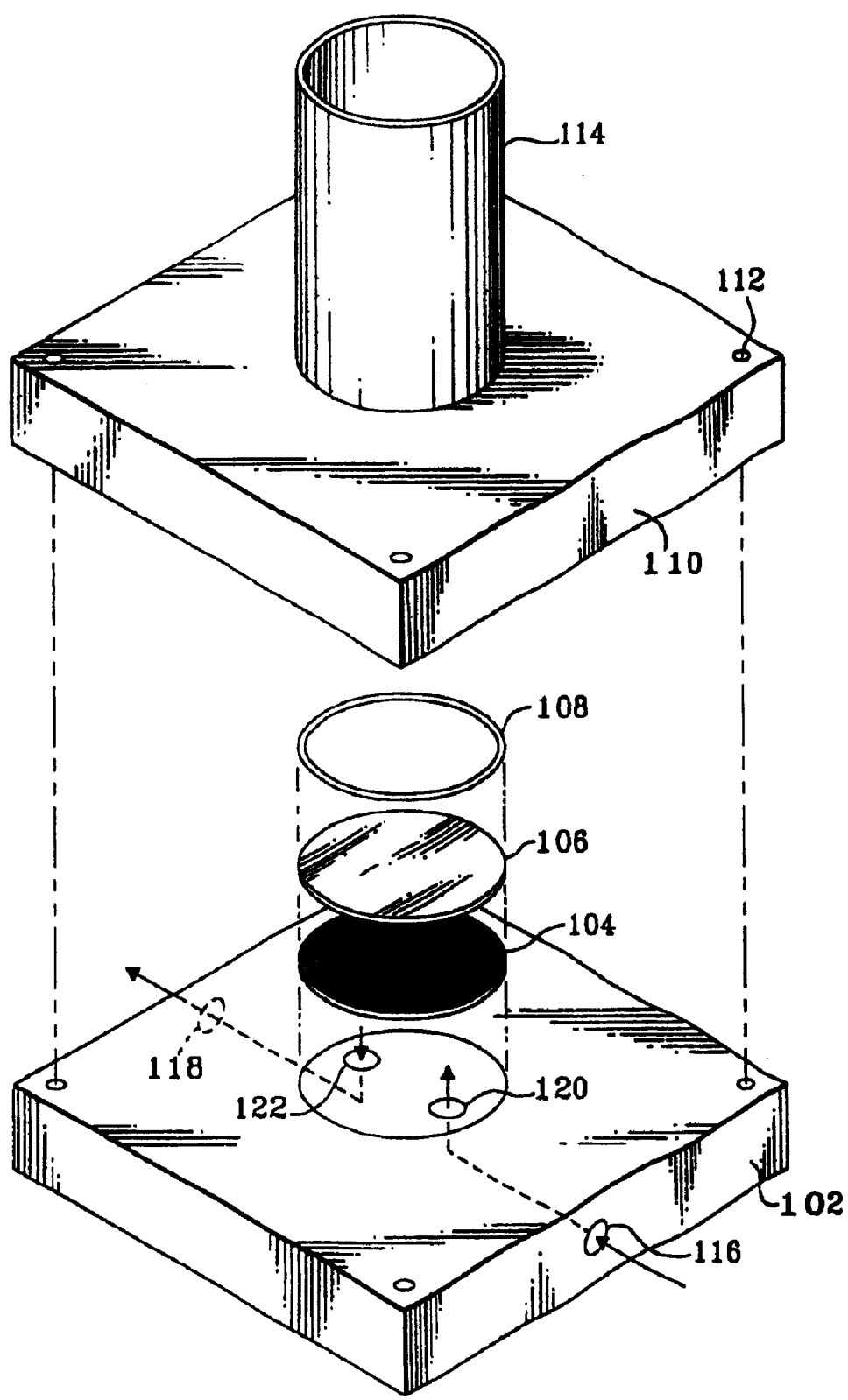
FIG. 3 is a generic view of the single-electrode bulk cell.

In FIG. 3, a simplified view of a single-electrode gas diffusion cell is illustrated. A catalyst that was identified as interesting in the combinatorial screening cell test can be tested "in bulk" under conditions more closely approximating those of an ultimate application. The term "bulk" as used herein is meant to describe an amount of catalyst greater than that used in the combinatorial screening test. The bulk catalyst is synthesized on or deposited on carbon paper as described above for the combinatorial screening method. The carbon paper supporting the catalyst, i.e., catalyst array support 106, may be placed on top of an optional carbon cloth disk 104. Disk 104 operates to diffuse reagent fluid across the entire catalyst deposit. Catalyst array support 106 and carbon cloth disk 104 are placed between the bulk-cell body 102 and an O-ring 108. It is preferred that the diameter of the volume of catalyst deposited on the catalyst array support matches that of the O-ring. The bulk cell cover 110 is placed over the assembly with the O-ring being seated in a groove in the bulk cell cover (not shown). The bulk cell body has fluid inlets 116 and 122 and fluid outlets 118 and 120, indicated by arrows, to allow the reactant feed gas to flow through the cell body, diffuse through the carbon cloth on the back side of the catalyst array support and contact the catalyst, diffuse back through the catalyst array support and cloth disk, and back out of the bulk cell body. Cloth disk 104 and catalyst array support 106 are positioned in alignment with fluid outlet 120 and fluid inlet 122 of bulk cell body 102. As with the combinatorial screening apparatus, the bottom of the carbon paper is preferably made hydrophobic with Teflon. The carbon paper is contacted as the working electrode in a three-electrode cell. The top cylindrical portion 114 of the bulk cell cover contains fluid such as a 0.5 M sulfuric acid electrolyte constantly blanketed with argon gas, and also contains the reference and counter electrodes (not shown). The voltage of the cell is changed using a potentiostat and the current is measured (not shown). The current voltage plot allows for comparison among catalysts according to their activity. The bulk testing cell allows for the use of a variety of feed gases including, but not limited to, hydrogen, oxygen, and simulated reformate gas.

When the combinatorial screening cell and the bulk testing cell are used sequentially in a series of experiments, a large number of catalysts can be studied for activity. The initial screening in the combinatorial screening cell identifies the general compositions that might be interesting for further investigation. The bulk testing cell allows those identified compositions to be further tested, compared, and ranked according to their activity under conditions that more closely mimic use in an actual fuel cell.

It must be emphasized that the examples below are merely illustrative of specific embodiments of the invention and are not intended as an undue limitation on the generally broad scope of the invention.

EXAMPLE 1

Compositions to be screened for electrocatalytic activity would be prepared according to the method described in Reddington E.; Sapienza A.; Gurau, G.; Rameshkrishnan V.; Sarangapani, S.; Smotkin, E. S.; Mallouk, T. E. Science, 1998, 280, 1735. Electrode arrays would be prepared in duplicate by printing precursor inks containing salts of the indicated metal (e.g., $H_2PtCl_6$, $RuCl_3$, $Na_2MoO_4$, $RhCl_3$, $K_2IrCl_6$) dissolved in a glycerol and water solution onto a Toray carbon catalyst array support. Inks would be delivered so that each "spot" in the array contained the same total number of moles of metal prior to the reduction step using an ink jet printer (e.g., an Apple Color Stylewriter 2500 where the pattern for each ink was drawn in grayscale with commercial drawing software). The spots would be reduced with a forty-fold molar excess of sodium borohydride, and the arrays would be washed repeatedly with deionized water.

The back of the catalyst array support would be made hydrophobic by coating with Teflon, and the catalyst array support would serve as the working electrode in a three-electrode system of the combinatorial screening cell. A mask would be placed over the catalyst bearing side of the catalyst array support so that only those portions of the catalyst array support having catalyst deposited thereon would be visible through the mask. Through the holes of the mask, catalysts would be contacted with an electrolyte solution maintained at a pH 3 and containing a Ni-3-pyridin-2-yl-,4,5,5>triazolo-<1,5-a>pyridine indicator. The catalyst array support would be conditioned for several minutes in a reformate stream, and the potential would be gradually increased from −150 mV vs. DHE (dynamic hydrogen reference electrode) until visible fluorescence was observed through the holes of the mask.

Bulk catalysts would be prepared in a similar way, except that the solutions of metal salts would be prepared by standard volumetric methods rather than by delivery from an ink-jet printer. For example, appropriate quantities of metal salts would be dissolved into water for an overall concentration of 2 mM and the pH adjusted to 9; a ten-fold excess of 5 wt % sodium borohydride would be added one drop at a time, and the precipitate would be washed with water and dried at 110° C. The solids would be tested on Toray carbon paper bulk catalyst support structures in the bulk catalyst cell of the present invention. The reagent gas would pass through the body of the bulk catalyst cell and through the bulk catalyst support structure to contact the catalyst. Current voltage curves would be recorded after an initial conditioning period, during which the catalyst would lose some activity, presumably because of the carbon monoxide poisoning.

EXAMPLE 2

Cathode screening may also be accomplished using the present invention. Compositions of interest would be prepared and printed only on Toray carbon paper as described in Example 1. The back of the catalyst array support would be made hydrophobic by coating with Teflon, and the catalyst array support would become the working electrode in the three-electrode system. A catalyst mask would be placed over the catalyst array support so that only those areas containing catalyst would be exposed. Oxygen would be diffused through the carbon paper to simulate the gas diffusion cathode environment found in a typical polymer electrolyte membrane (PEM) cell. The potential of the catalyst array support would be made progressively more negative, starting from a potential at which oxygen is not easily reduced. Phloxine B, active at basic pH values, would be used as the fluorescent indicator dye to indicate active catalytic compositions.

What is claimed is:

1. A combinatorial screening apparatus comprising:
 a) a cell body containing a fluid inlet;
 b) a fluid permeable, conductive, catalyst array support positioned adjacent to the cell body, said catalyst array support having multiple locations for supporting solids and having a first side and a second side;
 c) an independent catalyst mask positioned adjacent to the first side of the catalyst array support, said catalyst mask having material removed to form holes where the holes are in alignment with the multiple locations for supporting solids of the catalyst array support and thereby defining an unobstructed area above each location for supporting solids and masking the remainder of the catalyst array support;
 d) a cell cover positioned adjacent to the catalyst array support, said cell cover having material removed to allow for monitoring of the solids, and;
 e) an excitation source in alignment with the cell cover wherein the excitation source is an ultraviolet radiation source.

2. The apparatus of claim 1 further comprising a detector in alignment with the cell cover.

3. The apparatus of claim 1 further comprising a diffuser positioned between the catalyst array support and fluid inlet of the cell body.

4. The apparatus of claim 1 further comprising at least one fastener.

5. The apparatus of claim 1 further comprising a seal between each of the elements a–d of claim 1.

6. The apparatus of claim 1 further comprising an independent reagent mask positioned between the cell body and the catalyst array support, adjacent to the second side of the catalyst array support, said reagent mask having material moved to form holes where the holes are in alignment with the multiple locations for supporting solids of the catalyst array support and thereby defining a unobstructed area below each location for supporting solids and masking the remainder of the catalyst array support.

7. The apparatus of claim 1 further comprising a diffuser located between the cell body and the catalyst array support.

8. The apparatus of claim 1 wherein the catalyst array support is carbon paper.

9. The apparatus of claim 1 wherein the cell body is further characterized in having a fluid outlet.

10. The apparatus of claim 6 further comprising a diffuser located between the cell body and the reagent mask.

11. The apparatus of claim 6 further comprising a seal between the cell body and the reagent mask; a seal between the reagent mask and the catalyst arrays support; a seal between the catalyst array support and the catalyst mask; and a seal between the catalyst mask and the cell cover.

12. A combinatorial screening apparatus comprising:
 a) a cell body containing a fluid inlet;
 b) a fluid permeable, conductive, catalyst array support positioned adjacent to the cell body, said catalyst array support having multiple locations for supporting solids and having a first side and a second side;
 c) an independent Plexiglas catalyst mask positioned adjacent to the first side of the catalyst array support, said catalyst mask having material removed to form holes where the holes are in alignment with the multiple locations for supporting solids of the catalyst array support arid thereby defining an unobstructed area above each location for supporting solids and masking the remainder of the catalyst array support; and
 d) a cell cover positioned adjacent to the catalyst array support, said cell cover having material removed to allow for monitoring of the solids.

* * * * *

UNITED STATES PATENT AND TRADEMARK OFFICE
CERTIFICATE OF CORRECTION

PATENT NO. : 6,913,849 B2 Page 1 of 1
DATED : July 5, 2005
INVENTOR(S) : Thomas E. Mallouk et al.

It is certified that error appears in the above-identified patent and that said Letters Patent is hereby corrected as shown below:

Column 10,
Line 3, replace "moved" with -- removed --.
Line 34, replace "arid" with -- and --.

Signed and Sealed this

Sixth Day of September, 2005

JON W. DUDAS
*Director of the United States Patent and Trademark Office*